United States Patent [19]

Walker

[11] Patent Number: 4,562,838

[45] Date of Patent: Jan. 7, 1986

[54] ELECTROSURGERY INSTRUMENT

[76] Inventor: William S. Walker, 229 E. D Ave., Kalamazoo, Mich. 49004

[21] Appl. No.: 227,658

[22] Filed: Jan. 23, 1981

[51] Int. Cl.$^4$ ............................................. A61B 17/39
[52] U.S. Cl. ........................... 128/303.14; 128/303.17; 604/20; 604/22; 604/35; 219/230
[58] Field of Search ...................... 128/303.13–303.18, 128/275.1, 398, 23, 303.1; 219/230, 233, 234; 604/20–22, 35

[56] References Cited

U.S. PATENT DOCUMENTS

| | | | |
|---|---|---|---|
| 2,196,171 | 4/1970 | Ameser | 128/303.14 |
| 2,275,167 | 3/1942 | Bierman | 128/303.17 |
| 2,888,928 | 6/1959 | Seiger | 128/303.17 |
| 3,035,580 | 5/1962 | Guiorguiev | 128/303.18 |
| 3,595,239 | 7/1971 | Petersen | 128/303.14 |
| 3,614,414 | 10/1971 | Gores | 128/398 X |
| 3,648,001 | 3/1972 | Anderson et al. | 128/303.14 |
| 3,801,766 | 4/1974 | Morrison, Jr. | 128/303.14 |
| 3,847,153 | 11/1974 | Weissman | 128/303.14 |
| 3,906,955 | 9/1975 | Roberts | 128/303.17 |
| 3,920,022 | 11/1975 | Pastor | 128/303.13 |
| 4,074,718 | 2/1978 | Morrison, Jr. | 128/303.14 |
| 4,449,528 | 5/1984 | Auth et al. | 128/303.1 |

FOREIGN PATENT DOCUMENTS

| | | |
|---|---|---|
| 1007960 | 5/1957 | Fed. Rep. of Germany ......................... 128/303.17 |
| 57862 | 9/1953 | France ........................... 128/303.14 |

Primary Examiner—Lee S. Cohen
Attorney, Agent, or Firm—Dressler, Goldsmith, Shore, Sutker & Milnamow, Ltd.

[57] ABSTRACT

An electrosurgery instrument having ducts to direct a stream of fluid past the electrode to dissipate the smoke produced in surgery. The instrument can also be provided with a light-transmitting cable to illuminate a region around the electrode.

6 Claims, 9 Drawing Figures

U.S. Patent  Jan. 7, 1986  Sheet 1 of 2  4,562,838
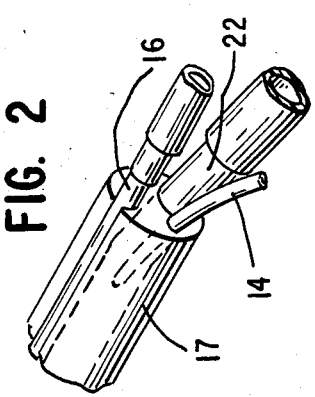
FIG. 2
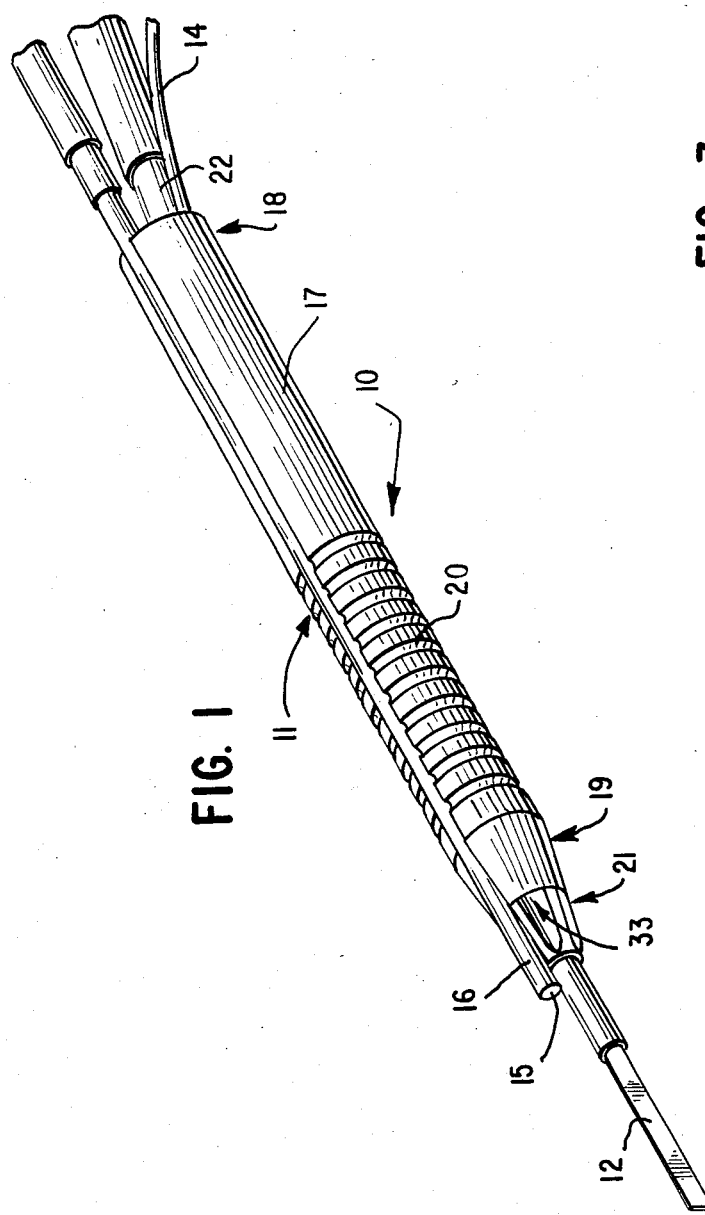
FIG. 1
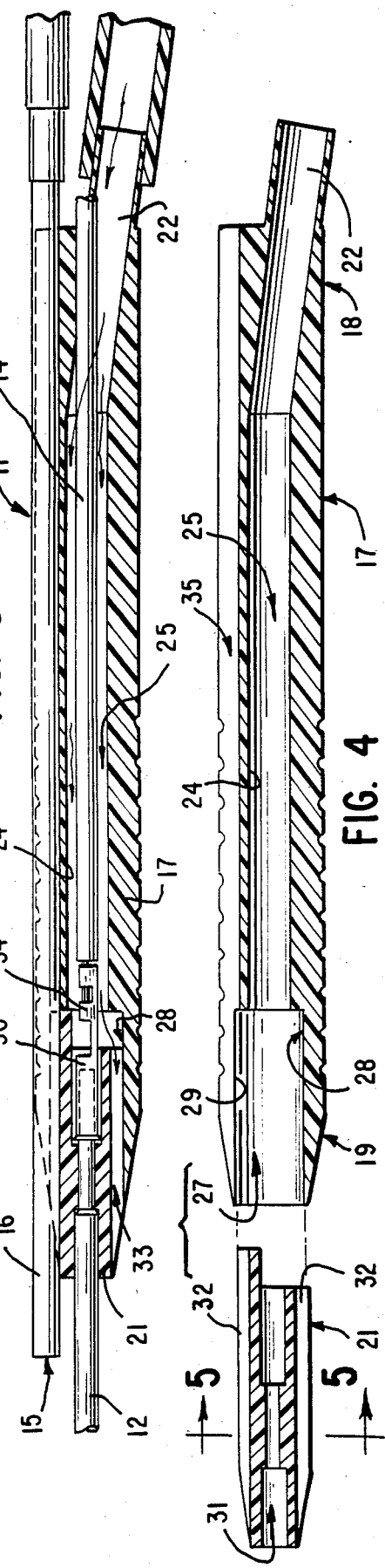
FIG. 3
FIG. 4

ELECTROSURGERY INSTRUMENT

TECHNICAL FIELD

This invention relates to surgical instruments and in particular instruments used in electrosurgery.

BACKGROUND OF THE INVENTION

Electrosurgery has been performed since the end of the nineteenth century and involves the use of the high frequency current to cut or coagulate tissue with an active electrode. A return electrode is placed in contact with the patient while a surgeon brings the active electrode either in contact with or adjacent to a body tissue. The high frequency current generates heat in the tissue, diathermy, which cuts the tissue and causes desiccation, the coagulation resulting in elongated cells shrunken by dehydration. By adjusting the current used, it is possible to cut tissue as with a knife or to coagulate the tissue to stop bleeding with or without also cutting the tissue.

In use, the large return electrode is positioned in contact with the body of the patient and connected to an electrosurgical power source. The electrosurgical power source produces a high frequency current in excess of 10,000 Hz with a preferred frequency being between 0.5 and 5 MHz. An undamped continuous sinusoidal waveform is best for strictly cutting tissue while a series of damped sinusoidal waves have been found best to achieve coagulation. Cutting with hemostasis is usually accomplished by using some combination of these waveforms.

As the small active electrode is brought into contact or close proximity with a body tissue the current at the tip of the electrode is concentrated over a small area giving a high current density, which coupled with the local electrical resistance of the tissue provides the effects necessary for cutting or coagulation. Heat is produced by the resistance to current flow as the electrical energy is absorbed and converted into thermal energy. The exact mechanisms and manner in which the area surrounding the active electrode heats, leading to a cutting effect, are not well understood at present and research is under way to better explain these phenomena.

At the tip of the electrode the current density and resistance are at their maximum, generating enough heat in a tissue for vaporization and pyrolysis. As the current spreads out through the body it is conducted over a much larger surface area, reducing the effective resistance and current density, and no significant heating occurs. The current completes its path back to the electrosurgery unit via the return electrode, also called the patient plate or dispersive electrode. This electrode always has a large surface area and is coated with an electrode paste to keep a low current density and resistance, thus avoiding areas of local heating and possible burns to the patient as the current leaves the body.

Electrosurgery is particularly useful when operating on highly vascularized tissue such as liver or muscle. Certain specialized uses for electrosurgery are so well established that they have become the standard technique, as in transurethral resection of the prostate and certain intracranial cutting procedures. However, the heat generated by electrosurgery produces much smoke distracting the surgeon and making it difficult for him to see what he is doing. Accordingly it becomes necessary to have an assistant present to blow away or aspirate the undesirable smoke. While such aid makes it possible for the operating surgeon to see, the necessity of either removing smoke or providing a light source distracts the operating surgeon and can result in the loss of concentration.

Accordingly it is desirable to provide an electrosurgery instrument which would improve the vision of the operating surgeon by removing the smoke and possibly also providing a local light source. It is also desirable that such an instrument be compact and easy to use without distracting the surgeon.

SUMMARY OF THE INVENTION

The present invention provides an electrosurgical instrument having ducts positioned to guide a fluid stream past an active electrode and adapted to hold a light-transmitting cable. In a preferred embodiment the instrument is disposable and comprises a hollow handle defining a fluid conduit which can be connected to a suction or a pressurized sterile air system. The handle also provides mounting for an electrical lead, one end of which is connected to the active electrode and the other end of which can be connected to an electro-surgical power source. The handle also provides mounting for the light-transmitting cable.

As the surgeon cuts or coagulates tissue, smoke is produced which distracts the surgeon and can interfere with his view of the operation. The smoke is removed by either introducing a positive pressure into the ducts of the instrument to blow the smoke away or by introducing a negative pressure into the ducts to aspirate the smoke in through the handle and into a vacuum system. Because the ducts are mounted in the handle of the instrument and in proximity to the active electrode, this smoke clearing system is effective without requiring any additional assistance or attention by the surgeon.

In another preferred embodiment, the handle comprises an elongated tube and a separate nose piece. The active electrode is mounted in the nose piece and is surrounded by a plurality of ducts. These ducts have a configuration adapted to guide a stream of air past that particular type of active electrode. Thus a nose piece retaining a blade electrode is provided with a certain configuration of ducts while another nose piece retaining, for example, an angled proctological ball electrode can be provided with a different duct arrangement as desired The nose pieces can be made interchangeable and disposable independently of the handle.

In yet another preferred embodiment the handle is provided with a mounting channel extending longitudinally along its outside surface that allows a light transmitting cable of a fiber optic system to be slidably received therein. This light transmitting cable can be adjusted by the surgeon so that illumination of the region surrounding the active electrode is maximized, thereby allowing the surgeon an enhanced view of the incision site. Thus this instrument not only removes the obstructing smoke from the surgeon's view but also improves that view by providing a local light source.

Numerous other advantages and features of the present invention will become readily apparent from the following detailed description of the invention, the accompanying examples, and the appended claims.

BRIEF DESCRIPTION OF THE DRAWINGS

FIG. 1 is a perspective view of an electrosurgical instrument having an active electrode, a light transmitting cable, and fluid and electrical connections;

FIG. 2 is a fragmentary perspective view of the proximal end of the electrosurgical instrument showing the attachment of a fiber optic cable as the light transmitting cable, and the fluid and electrical connections;

FIG. 3 is an enlarged cross-sectional view of an embodiment of the instrument showing an internal fluid conduit and a nose piece;

FIG. 4 is a cross-sectional exploded view, expanded to show features of the nose piece and handle body;

DESCRIPTION OF THE PREFERRED EMBODIMENT

Figure 5:
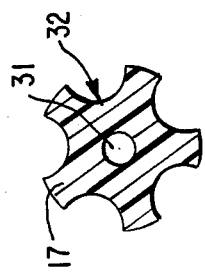
FIG. 5 is an enlarged cross-sectional view of the nose piece taken along plane 5—5 of FIG. 4.

While this invention is susceptible of embodiment in many different forms, there are shown in the drawings and will herein be described in detail preferred embodiments of the invention. It should be understood, however, that the present disclosure is to be considered as an exemplification of the principles of the invention and is not intended to limit the invention to the embodiments illustrated.

The precise shapes and sizes of the components herein described are not essential to the invention unless otherwise indicated. For ease of description the instrument of this invention will be described in a normal operating position. The choice of materials is dependent upon the particular application involved and other variables as those skilled in the art will appreciate.

Referring to FIGS. 1 and 2, electrosurgery instrument 10 comprises a handle 11, an active electrode such as a blade electrode 12 connected to an electrical lead 14 and a light transmitting cable 16. The active electrode is a conductor, usually metallic, and can be of any desired shape and size. The active electrode is connected to a power source (not shown) by means of an electrical lead 14 which passes through the insulating handle 11. The active electrode, which generally has a dull surface, is used to direct the high frequency current to the region of the patient that the surgeon wishes to affect.

The handle 11 is comprised of a hollow, elongated handle body or tube 17 having a proximal end 18 and a distal end 19, a nose piece 21 mounted in the tube, and a hose fitting 22. The handle 11 can also be provided with grip-enhancing serrations 20. The tube 17 has an inner surface 24 (FIGS. 3 and 4) defining a fluid conduit 25 and at the distal end 19 a tube cavity 27 whose wall surface 29 defines a seat 28. Either the nose piece 21 or tube 17, or both, can be made of an electrically non-conducting material as long as the surgeon is insulated from the electrode.

Figure 6:
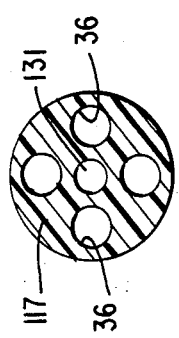
FIG. 6 is an enlarged cross-sectional view similar to FIG. 5, but showing an alternative nose piece construction.

The nose piece 21 is provided with a socket 31 to receive the active electrode 12 and has one or more flutes 32 around the periphery. The nose piece flutes 32 together with the tube seat 28 define ducts 33 which are in fluid communication with the fluid cavity 25 which in turn is in fluid communication with the hose fitting 22. The ducts 33 are positioned to guide a stream of fluid such as air past the active electrode 12 to remove or dissipate the smoke produced by use of the electrosurgery instrument. Alternatively as shown in FIG. 6, the ducts in the nose piece can be provided, by through passageways 36 or similar perforations along the length of the nose piece 117 housing central socket 131 for receiving the electrode.

The hose fitting 22 can either be connected to a sterile air pressure source or a vacuum source. If connected to an air pressure source, the air passes through the hose fitting 22 down the fluid conduit 25 which serves as a manifold to distribute the air flow through the passageways 36 or ducts 33 and past the active electrode 12. In a vacuum mode, the hose fitting 22 is connected to a vacuum system and the smoke produced around the active electrode is guided by a stream of air through the passageways 36 or ducts 33 through the fluid conduit 25 and out to the vacuum pump. Thus, either system removes or dissipates the smoke thereby avoiding distraction to the surgeon and providing him with a better view.

The nose piece 21 can be integral with the tube 17, and the electrode 12 is then removably received in the socket 31 and female socket 30 of the connector means 34 attached to the electrical lead 14. The fluid conduit can also serve as an access passageway for the electrical lead 14.

Preferably, the tube 17 is provided with a receptacle means or mounting channel 35 for slidably receiving the light transmitting cable 16 of a fiber optic system. The channel 35 (FIG. 4) holds a light emitting end 15 of the cable 16 adjacent to the active electrode to illuminate a region around the electrode.

Since active electrodes come in various shapes and sizes, it is desirable that the ducts of the nose piece be adapted to insure that the stream of fluid is properly guided around the active electrode. This is shown in an alternative embodiment in FIGS. 7, 8 and 9. In this particular embodiment the active electrode, shown as an angled proctological ball electrode 112, is held in the nose piece 121, and the flutes 132 have been modified to define ducts 133 to guide a stream of fluid past the electrode 112. The active electrode can be permanently fixed within the nose piece or removably retained therein, as desired. The light transmitting cable 116 has also been modified by angling the light emitting end 115 toward the active electrode so that the end directs the transmitted light to a region surrounding the ball electrode 112.

Figure 9:
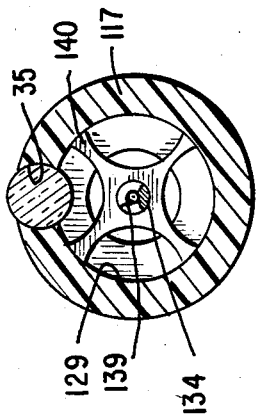
FIG. 9 is an enlarged cross-sectional view taken along plane 9—9 in FIG. 7.

A lead centering means 140 is mounted in the tube 117 to retain the connector means 134 in place as the nose piece 121 is removed. As best seen in FIG. 9, lead centering means 140 is a cross-like member provided with a central aperture 139 that receives and holds connector means 134 centered within cavity 127 and spaced from cavity wall surface 129. The electrode 112 is fixed in the nose piece 121 which is interchangeably mounted in the tube 117. To change electrodes, the surgeon removes one nose piece-electrode combination and replaces it with another. As the replacement is inserted, the electrode connects to the female socket 130 of the connecting means 134. This provides for easy interchangeability of the active electrode and nose piece.

Figure 7:
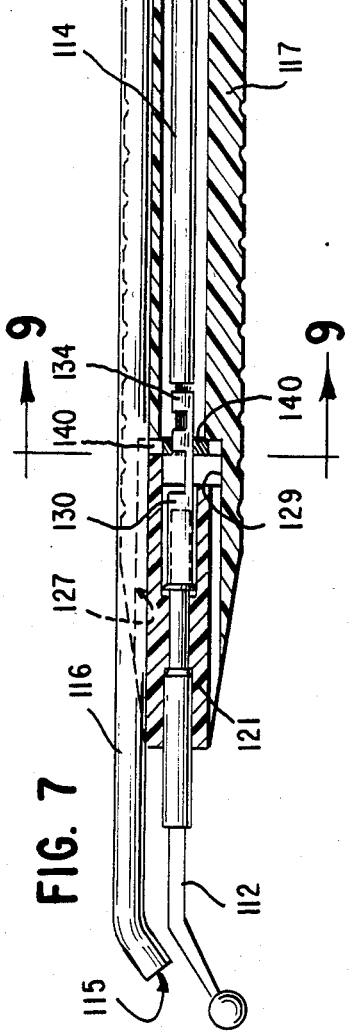
FIG. 7 is a cross-sectional view of an alternative embodiment of the invention showing a means to center the electrical lead which exits through the side of the handle and an alternative active electrode.
Figure 8:
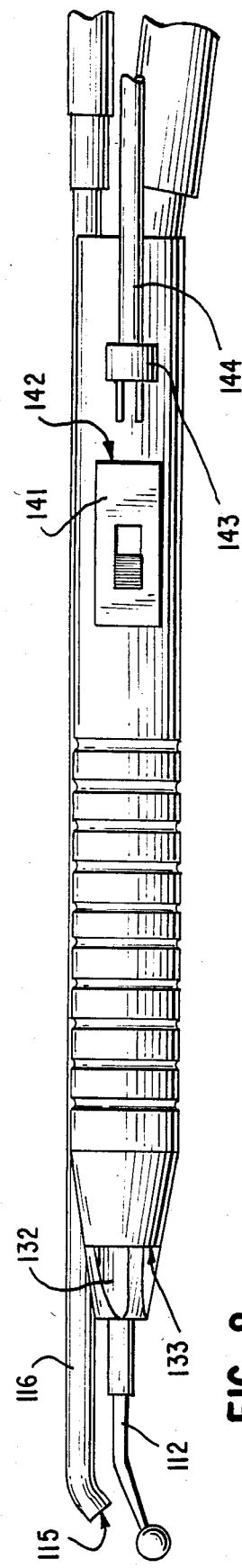
FIG. 8 is a side elevational view of the embodiment of FIG. 7 showing a switch means mounted on the handle, and a plug and a receptacle to connect the instrument to a power source.

As shown in FIGS. 7 and 8, the electrical lead 114 exits through the side of the tube 117 and is associated with a switch means 141 which controls the current directed to the active electrode 112. The switch means can be a slide switch or an intermittent push button to control the current. This allows the surgeon to adjust the type of current waveform used depending on the need to cut or coagulate. Mounted on the switch means 141 is a receptacle 142 which receives an electrical plug 143 connected to the wire 144 which leads to the power source.

In use, the surgeon holds the instrument 10 much as he would any surgical scapel. As the active electrode 12 is applied to the tissue, the smoke that is produced is removed by an air stream induced by pressure or vacuum at the ducts 33. This removes a potential obstruction to the surgeon's view caused by the smoke. The surgeon can also adjust the light transmitting cable 16 so that the light emitting end 15 is positioned to illuminate a region around the electrode. Thus not only is the obstruction to the surgeon's view removed in a manner that does not distract him but he is also provided with a light source which enables him to better view the procedure he is performing.

The foregoing specification is intended as illustrative only and is not to be taken as limiting. Still other variations within the spirit and scope of this invention are possible and will readily present themselves to those skilled in the art.

What is claimed is:

1. An electrosurgery instrument comprising:
   (a) a hollow, elongated tube having an inner surface defining an internal longitudinally extending fluid conduit, the tube also having a mounting channel extending longitudinally along the length of the tube;
   (b) an active electrode;
   (c) a nose piece mounted in the tube and holding the active electrode, the periphery of the nose piece being provided with at least one longitudinal flute which together with the inner surface of the tube defines a duct in fluid communication with the remainder of the fluid conduit, the duct being positioned to guide a fluid stream past the active electrode; the nose piece being constructed of an electrically nonconducting material;
   (d) an electrical lead connected to the active electrode; and
   (e) a light transmitting cable slidably received within the mounting channel with the light emitting end of the cable positioned adjacent to the active electrode to illuminate a region around the electrode.

2. The electrosurgery instrument of claim 1 including a switch means mounted on the tube and associated with the electrical lead to control the passage of electric current to the active electrode.

3. An electrosurgery scalpel handle comprising:
   (a) a hollow, elongated tube having an inner surface defining a longitudinal extending fluid conduit, the tube having a distal and a proximal end, the distal end defining a cavity having a surface defining a seat;
   (b) a nose piece mounted in the cavity and adapted to hold an active electrode, the periphery of the nose piece being provided with at least one longitudinal flute which together with the seat define a duct in fluid communication with the fluid conduit, the duct being positioned to guide a fluid stream past the active electrode; and
   (c) a hose fitting mounted on the proximal end of the tube in fluid communication with the fluid conduit; the tube also having a mounting channel extending longitudinally along the tube to slidably receive a light-transmitting cable and hold the cable with its light-emitting end adjacent to the nose piece so as to illuminate a region around the active electrode, the tube being constructed of an electrically nonconducting material.

4. The electrosurgery scalpel handle of claim 3 wherein the fluid conduit also serves as an access passageway for an electrical lead connected to the active electrode.

5. The electrosurgery scalpel handle of claim 3 including a switch means mounted on the tube to regulate the flow of current to the active electrode.

6. The electrosurgery scalpel handle of claim 3 including grip enhancing serrations around the periphery of the tube.

* * * * *